US007220881B2

United States Patent
Shiigi et al.

(10) Patent No.: US 7,220,881 B2
(45) Date of Patent: May 22, 2007

(54) PROCESS FOR PRODUCTION OF ACID ANHYDRIDE

(75) Inventors: Hirofumi Shiigi, Yamaguchi (JP); Eiji Ohshima, Yamaguchi (JP); Masao Yamaguchi, Yamaguchi (JP)

(73) Assignee: Tokuyama Corporation, Yamaguchi (JP)

( * ) Notice: Subject to any disclaimer, the term of this patent is extended or adjusted under 35 U.S.C. 154(b) by 197 days.

(21) Appl. No.: 10/485,129

(22) PCT Filed: Jul. 24, 2002

(86) PCT No.: PCT/JP02/07461

§ 371 (c)(1),
(2), (4) Date: Jun. 28, 2004

(87) PCT Pub. No.: WO03/011818

PCT Pub. Date: Feb. 13, 2003

(65) Prior Publication Data

US 2004/0242929 A1  Dec. 2, 2004

(30) Foreign Application Priority Data

Aug. 1, 2001  (JP)  ............................. 2001-233382
Jul. 8, 2002  (JP)  ............................. 2002-198475

(51) Int. Cl.
*V07C 51/56*  (2006.01)
(52) U.S. Cl. .................................................... 562/895
(58) Field of Classification Search ................ 562/887, 562/889, 895, 896, 897
See application file for complete search history.

(56) References Cited

U.S. PATENT DOCUMENTS 5,461,162 A * 10/1995 Ho et al. .................... 548/188

FOREIGN PATENT DOCUMENTS

JP  2002-226421  8/2002

OTHER PUBLICATIONS

Nangia et al., Journal of Chemical Research, Synopses (1984), (3), 100 (CASREACT online citation on STN [retrieved Feb. 27, 2006] ACS, Columbus, OH, USA).*
Lynch et al., J. Org. Chem.; 1989; 54(16) pp. 3792-3796.*
Brewster, et al.; "Dehybrations with Aromatic Sulfonyl Halides in Pyridine. A Conventional Method for the Preparation of Esters"; Journal of American Chemical Society; 1955, vol. 77, pp. 6214-6215.
Urbanski, et al.; "Reactions of Carboxylic Acids in Presence of Arenesulfonyl Chlorides and Tertiary Amines. Part I. Formation of Carboxylic Acid Anhydrides"; Polish Journal of Chemistry; 1978, vol. 52, No. 2, pp. 301-314.
Nangia, et al.; "A Mild Method for Carboxy-group Activation and Synthesis of Carboxylic Anhydrides"; Journal of Chemical Research, 1984, vol. 3; Synopses.
Wirth, David D.; "Carboxylic Sulfonic Mixed Anhydrides: General Utility and Application to the Synthesis of Ceftazidime"; Tetrahedron, 1993, vol. 49, No. 8, pp. 1535-1540.

* cited by examiner

*Primary Examiner*—Karl Puttlitz
(74) *Attorney, Agent, or Firm*—Norris McLaughlin & Marcus PA

(57) ABSTRACT

According to the present invention there is provided a process for producing an acid anhydride by reacting a carboxylic acid, preferably a carboxylic acid having a polymerizable group, with a sulfonyl halide compound in the presence of a tertiary amine or in the presence of a tertiary amine and an inorganic base, wherein the tertiary amine or the tertiary amine and the inorganic base are used in an amount of 0.9 to 1.2 equivalents relative to the acid generated from the sulfonyl halide compound.

6 Claims, No Drawings

PROCESS FOR PRODUCTION OF ACID ANHYDRIDE

TECHNICAL FIELD

The present invention relates to a process for producing an acid anhydride industrially. Acid anhydrides are useful as an acylating agent used in amidation, esterification, etc.

BACKGROUND ART

As the process for producing an acid anhydride, there has been a process which comprises reacting a low-molecular acid anhydride such as acetic anhydride with a high-molecular carboxylic acid [for example, J. Am. Chem. Soc. 63 699 (1941)], or a process which comprises reacting a low-molecular acid anhydride with a high-molecular carboxylic acid chloride to form a high-molecular acid anhydride (for example, JP-A-5-339194). In these processes, the low-molecular carboxylic acid formed as a by-product or a carboxylic acid chloride is removed by azeotropic distillation with a solvent. With these processes, however, it is difficult to produce a low-molecular acid anhydride and the yield thereof is low. Further, this process has a problem in that it is unapplicable to production of an acid anhydride which is thermally unstable.

As the process for producing a low-molecular acid anhydride, there is known a process which comprises reacting an acid halide with a carboxylic acid and wherein the inorganic acid formed as a by-product is removed (for example, JP-A-9-104642) or a process which comprises reacting an acid halide with a metal carboxylate and wherein the metal salt formed is removed [for example, J. Org. Chem. 60(7) 2271 (1995)]. Even with these processes, however, the yield of the acid anhydride obtained is not satisfactory. Further, the reaction using an acid halide is inferior in the safety of reaction.

Meanwhile, as the process for producing a low-molecular acid anhydride at a good yield, there is known a process which comprises reacting a carboxylic acid with methanesulfonyl chloride in the presence of triethylamine [J. Chem. Res., Synop. 3 100 (1984)]. In this process, 2 equivalents of a carboxylic acid is reacted using 2.1 equivalents of methanesulfonyl chloride [therefore, the acids (hydrochloric acid and methanesulfonic acid) formed by the reaction with methanesulfonyl chloride become 2.1 equivalents] and 3.33 equivalents of triethylamine (this trimethylamine amount becomes 1.67 equivalents relative to the acids formed from methanesulfonyl chloride). In this reaction, triethylamine is used in an amount fairly larger than the stoichiometric amount required for the raw material carboxylic acid and methanesulfonyl chloride in order to accelerate the reaction. This reaction is conducted at −15° C. using tetrahydrofuran as a solvent.

After the reaction, tetrahydrofuran is distilled off under reduced pressure; ethyl acetate is added to the residue for dissolution; and the ethyl acetate phase is washed with an aqueous sodium hydrogencarbonate solution. Thereafter, the ethyl acetate phase is dried over anhydrous sodium sulfate, after which the solvent therein is distilled off to obtain an intended acid anhydride.

The above reaction is highly reactive and tends to give rise to a side reaction. As a result, the yield tends to be inferior and the reaction has a room for improvement. Particularly when the carboxylic acid is a polymerizable group-containing carboxylic acid such as acrylic acid or methacrylic acid [hereinafter the both are referred to as (meth)acrylic acid], a fairly large proportion of the acid anhydrides obtained is a polymer(s), which greatly reduces the yield of an intended product.

Further in the above process using a large amount of triethylamine, washing with water is conducted after the reaction in order to remove triethylamine from the product; however, the compound has a strong odor and is unable to remove sufficiently.

Furthermore, a triethylamine salt is contained in a large amount in the waste solution generated from the above washing with water, which poses a problem of waste solution disposal.

Thus, it is desired to develop a process for producing an acid anhydride, which can produce an acid anhydride at a high yield and a high purity, wherein the purification of intended product from reaction mixture is easy, and wherein the waste solution disposal is easy as well.

DISCLOSURE OF THE INVENTION

The present inventors continued an intensive study in order to achieve the above task. As a result, it was found out that the above task can be achieved by allowing a particular amount of a tertiary amine or particular amounts of a tertiary amine and an inorganic base to be present in a reaction system of a carboxylic acid and a sulfonyl halide compound. The present invention has been completed based on the finding.

The present invention lies in a process for producing an acid anhydride by reacting a carboxylic acid with a sulfonyl halide compound in the presence of a tertiary amine, wherein the amount of the tertiary amine used is 0.9 to 1.2 equivalents relative to the acids generated from the sulfonyl halide compound.

The present invention lies also in a process for producing a carboxylic acid anhydride by reacting 1 mole of a carboxylic acid with 0.4-0.6 mole of a sulfonyl halide compound in the presence of a tertiary amine and an inorganic base, wherein the total amount of the tertiary amine and inorganic base used is 0.9 to 1.2 equivalents (the amount of the tertiary amine is at least 0.05 equivalent) relative to the acids generated from the sulfonyl halide compound.

BEST MODE FOR CARRYING OUT THE INVENTION

In the present invention, the carboxylic acid as a starting raw material comprises a hydrocarbon group and a carboxyl group bonded thereto and, as the carboxylic acid, there can be used known fatty acids, known alicyclic carboxylic acids, known aromatic carboxylic acids, etc. with no restriction. The carboxylic acid preferably has 1 to 20 carbon atoms.

The hydrocarbon group bonded to the carboxyl group of the carboxylic acid may have a substituent. As the substituent, there can be mentioned, for example, halogen atoms such as chlorine, fluorine, bromine, iodine and the like; alkoxy groups such as methoxy group, ethoxy group, propoxy group, isopropoxy group, butoxy group, isobutoxy group, sec-butoxy group, tert-butoxy group, pentyloxy group and the like; cycloalkyloxy groups such as cyclopropoxy group, cyclohexyl group and the like; aralkoxy groups such as benzyloxy group and the like; aryl groups such as phenyl group, toluyl group and the like; nitro group; amino group; imino group; carbamoyl group; hydrazinocarbamoyl group; cyano group; isocyano group; cyanato group; isocyanato group; thiocyanato group; isothiocyanato group; formyl group; thioformyl group; oxo group; thioxo group;

hydroxy group; and mercapto group. Two or more of these substituents may be bonded to the hydrocarbon group.

As specific examples of the carboxylic acid, the followings can be cited. These specific examples exclude those carboxylic acids having a polymerizable group, preferably used as a raw material in the present production process described below.

Fatty acids such as formic acid, acetic acid, propionic acid, butyric acid, valeric acid, pivalic acid, caproic acid, heptanoic acid, caprylic acid, capric acid, lauric acid, myristic acid, palmitic acid, stearic acid, oleic acid, linolic acid, linoleic acid, crotonic acid, 3-methylcrotonic acid, propiolic acid, isocrotonic acid, elaidic acid, propiolic acid and the like; alicyclic carboxylic acids such as cyclopropanecarboxylic acid, cyclobutanecarboxylic acid, cyclohexanecarboxylic acid, cycloheptanecarboxylic acid, cyclooctanecarboxylic acid, cyclohexenecarboxylic acid and the like; aromatic carboxylic acids such as phenylacetic acid, benzoic acid, o-toluylic acid, m-toluylic acid, p-toluylic acid, o-nitrobenzoic acid, m-nitrobenzoic acid, p-nitrobenzoic acid, o-methoxybenzoic acid, m-methoxybenzoic acid, p-methoxybenzoic acid, o-chlorobenzoic acid, m-chlorobenzoic acid, p-chlorobenzoic acid, 1-naphthalenecarboxylic acid, 2-naphthalenecarboxylic acid, cis-cinnamic acid, trans-cinnamic acid, propiolic acid and the like; and heterocyclic carboxylic acids such as tetrahydrofurancarboxylic acid, pyromucic acid, 3-pyromucic acid and the like.

In the present invention, there can be also be suitably used oxo acids such as glyoxylic acid, pyruvic acid, acetoacetic acid, meso-oxalic acid, oxalic acid, levulinic acid and the like; amino acid derivatives wherein the amino group is protected; and so forth. These carboxylic acids may be used as a mixture.

As the carboxylic acid having a polymerizable group, there is ordinarily used a carboxylic acid represented by the following formula (1)

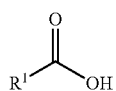

(1)

(wherein $R^1$ is an optionally substituted polymerizable unsaturated hydrocarbon group).

As to the polymerizable unsaturated hydrocarbon group, there is no particular restriction, and known hydrocarbon groups capable of giving rise to addition polymerization can be mentioned. As specific examples, there can be mentioned aliphatic hydrocarbon groups of 1 to 15 carbon atoms, having a polymerizable double bond, such as vinyl group, allyl group, isopropenyl group, 2-propenyl group, 3-butenyl group, 3-methyl-3-butenyl group, 1,3-butadienyl group, 4-pentenyl group, 4-methyl-4-pentenyl group, 1,4-pentadienyl group, 2,4-pentadienyl group, 5-hexenyl group, 5-methyl-5-hexenyl group, 1,5-hexadienyl group, 2,5-hexadienyl group, 3,5-hexadienyl group, 6-heptenyl group, 6-methyl-6-heptenyl group, 7-octenyl group, 7-methyl-7-octenyl group, 1-propenyl group, 2-butenyl group and the like; alicyclic hydrocarbon groups of 1 to 15 carbon atoms, having a polymerizable double bond, such as o-vinylcyclohexyl group, m-vinylcyclohexyl group, p-vinylcyclohexyl group, vinylcyclopropyl group, vinylcyclooctyl group and the like; aromatic hydrocarbons of 6 to 15 carbon atoms, having a polymerizable double bond, such as o-vinylphenyl group, m-vinylphenyl group, p-vinylphenyl group, styryl group and the like; and hydrocarbon groups of 1 to 15 carbon atoms, having a polymerizable triple bond, such as ethynyl group, 2-propynyl group, 3-butynyl group, 4-pentynyl group, 5-hexynyl group, 6-heptynyl group, 7-octynyl group and the like. Of these, there are particularly preferred, from an industrial standpoint, hydrocarbon groups having a polymerizable double bond at the molecular end, such as vinyl group, allyl group, isopropenyl group, vinylphenyl group and the like.

These polymerizable unsaturated hydrocarbon groups may have a substituent such as mentioned above.

As specific examples of the carboxylic acid having a polymerizable bond, there can be mentioned acrylic acid, methacrylic acid, o-vinylcyclohexanecarboxylic acid, m-vinylcyclohexanecarboxylic acid, p-vinylcyclohexanecarboxylic acid, o-vinylbenzoic acid, m-vinylbenzoic acid, p-vinylbenzoic acid, vinylacetic acid, 2-propenylcarboxylic acid, 3-butenylcarboxylic acid, 3-methyl-3-butenylcarboxylic acid, 1,3-butadienylcarboxylic acid, 4-pentenylcarboxylic acid, 4-methyl-4-pentenylcarboxylic acid, 1,4-pentadienylcarboxylic acid, 2,4-pentadienylcarboxylic acid, 5-hexenylcarboxylic acid, 5-methyl-5-hexenylcarboxylic acid, 1,5-hexadienylcarobxylic acid, 2,5-hexadienylcarboxylic acid, 3,5-hexadienylcarboxylic acid, 6-heptenylcarboxylic acid, 6-methyl-6-heptenylcarboxylic acid, 7-octenylcarboxylic acid, 7-methyl-7-octenylcarboxylic acid, o-vinylcyclohexylcarboxylic acid, m-vinylcyclohexylcarboxylic acid, p-vinylcyclohexylcarboxylic acid, o-vinylphenylcarboxylic acid, m-vinylphenylcarboxylic acid, p-vinylphenylcarboxylic acid, ethynylcarboxylic acid, 2-propynylcarboxylic acid, 3-butynylcarboxylic acid, 4-pentynylcarbxylic acid, 5-hexynylcarboxylic acid, 6-hepthynylcarboxylic acid, 7-octynylcarboxylic acid and atropic acid. These carboxylic acids may be used as a mixture of two or more kinds. Of these, acrylic acid and methacrylic acid are particularly important industrially.

As described in the section of "Background Art", in the conventional processes, carboxylic acids having a polymerizable group, when reacted with a sulfonyl halide compound in the presence of a tertiary amine, give rise to even a polymerization reaction, resulting in a large reduction in yield of acid anhydride. According to the present invention, however, the polymerization reaction of the carboxylic acid having a polymerizable group is strikingly suppressed as described later, making it possible to obtain an acid anhydride at a high yield.

As the sulfonyl halide compound which is another starting raw material in the present invention, there can be used known such compounds with no restriction. In general, there can be used compounds represented by the following formula (2)

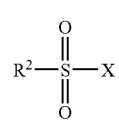

(2)

(wherein $R^2$ is an alkyl group, a cycloalkyl group, an aralkyl group or an aryl group, and X is a halogen atom).

When $R^2$ is an alkyl group, the alkyl group may be straight chain or branched chain. The carbon atoms are preferably 1 to 10, more preferably 3 to 8 for the high reactivity. As specific examples, there can be shown methyl group, ethyl group, n-propyl group, isopropyl group, n-butyl group, isobutyl group, tert-butyl group, n-pentyl group, isopentyl group, tert-pentyl group, n-hexyl group, isohexyl group, tert-hexyl group, n-heptyl group, isoheptyl group, tert-heptyl group, n-octyl group, isooctyl group and tert-octyl group.

The cycloalkyl group preferably has 3 to 8 carbon atoms. As specific examples, there can be shown cyclopropyl group, cyclobutyl group, cyclohexyl group, cycloheptyl group and cyclooctyl group.

The aralkyl group preferably has 7 to 12 carbon atoms. As specific examples, there can be shown benzyl group, phenethyl group, dimethylbenzyl group and naphthylmethyl group.

The aryl group preferably has 6 to 12 carbon atoms, and there can be shown phenyl group, tolyl group and naphthyl group.

In the formula (2), X is a halogen atom. As the halogen atom, there can be mentioned fluorine atom, chlorine atom, bromine atom and iodine atom. Chlorine atom is most preferred for the availability.

As specific examples of the sulfonyl halide compound having a chemical structure of the formula (2), the following compounds can be shown.

Methanesulfonyl fluoride, methanesulfonyl chloride, methanesulfonyl bromide, methanesulfonyl iodide, ethanesulfonyl fluoride, ethanesulfonyl chloride, ethanesulfonyl bromide, ethanesulfonyl iodide, n-propanesulfonyl fluoride, n-propanesulfonyl chloride, n-propanesulfonyl bromide, n-propanesulfonyl iodide, isopropanesulfonyl fluoride, isopropanesulfonyl chloride, isopropanesulfonyl bromide, isopropanesulfonyl iodide, n-pentanesulfonyl fluoride, n-pentanesulfonyl chloride, n-pentanesulfonyl bromide, n-pentanesulfonyl iodide, isopentanesulfonyl fluoride, isopentanesulfonyl chloride, isopentanesulfonyl bromide, isopentanesulfonyl iodide, tert-pentanesulfonyl fluoride, tert-pentanesulfonyl chloride, tert-pentanesulfonyl bromide, tert-pentanesulfonyl iodide, n-hexanesulfonyl fluoride, n-hexanesulfonyl chloride, n-hexanesulfonyl bromide, n-hexanesulfonyl iodide, isohexanesulfonyl fluoride, isohexanesulfonyl chloride, isohexanesulfonyl bromide, isohexanesulfonyl iodide, tert-hexanesulfonyl fluoride, tert-hexanesulfonyl chloride, tert-hexanesulfonyl bromide, tert-hexanesulfonyl iodide, n-heptanesulfonyl fluoride, n-heptanesulfonyl chloride, n-heptanesulfonyl bromide, n-heptanesulfonyl iodide, isoheptanesulfonyl fluoride, isoheptanesulfonyl chloride, isoheptanesulfonyl bromide, isoheptanesulfonyl iodide, tert-heptanesulfonyl fluoride, tert-heptanesulfonyl chloride, tert-heptanesulfonyl bromide, tert-heptanesulfonyl iodide, n-octanesulfonyl fluoride, n-octanesulfonyl chloride, n-octanesulfonyl bromide, n-octanesulfonyl iodide, isooctanesulfonyl fluoride, isooctanesulfonyl chloride, isooctanesulfonyl bromide, isooctanesulfonyl iodide, tert-octanesulfonyl fluoride, tert-octanesulfonyl chloride, tert-octanesulfonyl bromide, tert-octanesulfonyl iodide, cyclopropanesulfonyl fluoride, cyclopropanesulfonyl chloride, cyclopropanesulfonyl bromide, cyclopropanesulfonyl iodide, cyclobutanesulfonyl fluoride, cyclobutanesulfonyl chloride, cyclobutanesulfonyl bromide, cyclobutanesulfonyl iodide, cyclopentanesulfonyl fluoride, cyclopentanesulfonyl chloride, cyclopentanesulfonyl bromide, cyclopentanesulfonyl iodide, cyclohexanesulfonyl fluoride, cyclohexanesulfonyl chloride, cyclohexanesulfonyl bromide, cyclohexanesulfonyl iodide, cycloheptanesulfonyl fluoride, cycloheptanesulfonyl chloride, cycloheptanesulfonyl bromide, cycloheptanesulfonyl iodide, cyclooctanesulfonyl fluoride, cyclooctanesulfonyl chloride, cyclooctanesulfonyl bromide, cyclooctanesulfonyl iodide, benzenesulfonyl fluoride, benzenesulfonyl chloride, benzenesulfonyl bromide, benzenesulfonyl iodide, o-toluenesulfonyl fluoride, o-toluenesulfonyl chloride, o-toluenesulfonyl bromide, o-toluenesulfonyl iodide, m-toluenesulfonyl fluoride, m-toluenesulfonyl chloride, m-toluenesulfonyl bromide, m-toluenesulfonyl iodide, p-toluenesulfonyl fluoride, p-toluenesulfonyl chloride, p-toluenesulfonyl bromide, and p-toluenesulfonyl iodide.

Of these, preferred are compounds wherein $R^2$ is an alkyl group or an aryl group and X is chlorine, such as methanesulfonyl chloride, benzenesulfonyl chloride, p-toluenesulfonyl chloride and the like, because they have a low odor, give good workability, are easy to procure, and give a highly water-soluble salt after the reaction.

The tertiary amine used in the reaction can be any compound having a tertiary amino group, and there can be used aliphatic amines, alicyclic amines and aromatic amines with no restriction. The tertiary amine may be those having a plurality of amino groups in the molecule, such as diamine and the like. The tertiary amine may also be a cyclic amine containing nitrogen atom as a constituent atom of the heterocycle. As specific examples of the tertiary amine, the following compounds can be shown.

Aliphatic tertiary amines and alicyclic tertiary amines such as triethylamine, tributylamine, dimethylisopropylamine, dimethylcyclohexylamine, N,N,N',N'-tetramethylethylenediamine, N,N,N',N'-tetramethylpropanediamine and the like; aromatic amines such as N,N-dimethylaniline, N,N-diethylaniline, N,N-dimethylbenzylamine, N,N-diethylbenzylamine and the like; and cyclic amines such as pyridine, 4-methylmorpholine, 4-ethylmorpholine, 4-butylmorpholine, N-methylpyrrolidine, N-ethylpyrrolidine, N-methylpiperidine, N-ethylpiperidine, N-methylindoline, N-methylisoindoline, N-methylindole, N-methylisoindole, N-methylpyrrole and the like.

Of these, preferred are tertiary amines wherein alkyl groups of 2 to 4 carbon atoms are bonded to the nitrogen atom, such as triethylamine, tributylamine and the like and cyclic amines such as pyridine, 4-methylmorpholine, 4-ethylmorpholine, 4-butylmorpholine, N-methylpiperidine, N-ethylpiperidine, N-butylpiperazine, N-methylpyrrolidine and the like, because they give a highly water-soluble salt (described later) generated after the reaction and are easy to separate by washing.

The important point of the present invention lies in that in reacting the carboxylic acid with the sulfonyl halide compound in the presence of the tertiary amine, the use amount of the tertiary amine is strictly specified at 0.9 to 1.2 equivalents, preferably at 0.9 to 1.1 equivalents relative to the acids (stoichiometric amount) generated from the sulfonyl halide compound.

In the present reaction, the sulfonyl chloride compound enables formation of 1 mole of an acid anhydride from 2 moles of a carboxylic acid and per se changes into sulfonyl ion and halogen ion. These ions form acids and the acids react with a tertiary amine to form a hydrogen halide salt and a sulfonic acid salt. The use amount of the tertiary amine, specified by the present invention indicates the equivalent of the tertiary amine used as a base relative to the equivalents (stoichiometric amounts) of the acids generated from the sulfonyl chloride compound.

By thus specifying the use amount of the tertiary amine at a small amount and yet in a narrow range which roughly corresponds to the equivalents of the acids generated, it is possible to suppress the formation of by-products reliably. As a result, an acid anhydride of high purity can be produced at a high yield. Further, since the tertiary amine remains in a small amount in the mixture after the reaction, the purification of the produced acid anhydride and the operation of disposal of the waste solution are improved greatly.

When the use amount of the tertiary amine is larger than 1.2 equivalents relative to the acids generated from the sulfonyl halide compound, by-products tend to be formed and the yield of the acid anhydride decreases. This tendency is particularly striking when the carboxylic acid used is a carboxylic acid having a polymerizable unsaturated hydrocarbon group. Meanwhile, when the use amount of the tertiary amine is smaller than 0.9 equivalent relative to the acids generated from the sulfonyl halide compound, the yield of the acid anhydride decreases.

In the present invention, it is preferred that the tertiary amine is used in combination with an inorganic base in the reaction of the carboxylic acid with the sulfonyl halide compound. The combination use of the inorganic base can achieve the object of the present invention more preferably. The total use amount of the tertiary amine and the inorganic base is 0.9 to 1.2 equivalents, preferably 0.9 to 1.1 equivalents relative to the acids (stoichiometric amounts) generated from the sulfonyl halide compound. It is also preferred that the amount of the tertiary amine is at least 0.05 equivalent, preferably 0.1 to 0.9 equivalent of the total use amount of the tertiary amine and the inorganic base.

The inorganic base, when used alone, ordinarily shows substantially no action for promoting the reaction for formation of the acid anhydride. However, when the inorganic base and the tertiary amine are used in combination in the reaction, first the tertiary amine promotes the reaction; then, the inorganic base acts on the hydrogen halide salt and sulfonic acid salt of the tertiary amine, both generated with the progress of the reaction, whereby the inorganic base replaces the tertiary amine. As a result, a tertiary amine is liberated from the hydrogen halide salt and the sulfonic acid salt, and the liberated tertiary amine is reused in the reaction between the carboxylic acid and the sulfonyl halide compound.

The reaction mechanism thereof is presumed to be as follows. That is, the reaction between the carboxylic acid and the sulfonyl halide compound in the presence of the tertiary amine alone (no inorganic base is present) is considered to proceed violently according to the following two steps (A) and (B). In the following scheme, triethylamine is used as the tertiary amine.

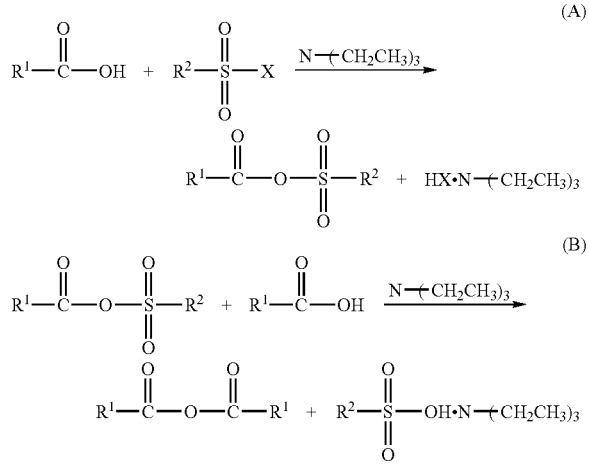

In contrast, when the inorganic base is allowed to co-exist in the reaction system, it is presumed that the once-formed hydrogen halide salt and sulfonic acid salt of the tertiary amine are returned to a free tertiary amine (regeneration of tertiary amine) owing to the presence of the inorganic base, as shown in the following formula. In this reaction, explanation is made using sodium carbonate as the inorganic base.

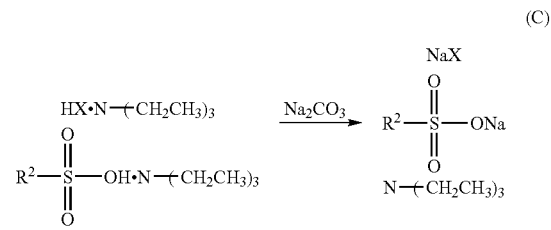

As a result, the tertiary amine consumed in the reaction is regenerated successively even when the use amount of the tertiary amine is reduced; therefore, the reaction continues mildly and can proceed to the last. Further, by greatly reducing the use amount of the tertiary amine to a level mentioned above, the reaction proceeds mildly, achieving a reaction of very high stability. As a result, an acid anhydride of higher purity can be obtained at a high yield.

When the total use amount of the tertiary amine and the inorganic base is larger than 1.2 equivalents of the acids generated from the sulfonyl halide compound, side reactions tend to take place, reducing the yield of the acid anhydride.

When the total use amount of the tertiary amine and the inorganic base is smaller than 0.9 equivalent of the acids generated from the sulfonyl halide compound, the reaction rate is smaller, resulting in a reduction in acid anhydride yield and a longer reaction time.

When the use amount of the tertiary amine in the total use amount of the tertiary amine and the inorganic base is smaller than 0.05 equivalent, the reaction rate is smaller, resulting in a reduction in acid anhydride yield and a longer reaction time.

As the inorganic base, any known compound can be used. Specifically, there can be mentioned, for example, sodium hydroxide, potassium hydroxide, lithium hydroxide, sodium carbonate, potassium carbonate, lithium carbonate, sodium hydrogencarbonate, potassium hydrogencarbonate, lithium hydrogencarbonate, calcium hydroxide, magnesium hydroxide, calcium carbonate and magnesium carbonate. Of these, preferred are carbonates with which the hydrolysis of the acid anhydride formed takes place hardly, such as sodium carbonate, calcium carbonate, potassium carbonate, lithium carbonate, sodium hydrogencarbonate, calcium hydrogencarbonate, lithium hydrogencarbonate and the like.

In the present invention, the use amount of the sulfonyl halide compound is not particularly restricted. The use amount of the sulfonyl halide compound is ordinarily preferred to be 0.4 to 0.6 mole per mole of the carboxylic acid and, in order to reduce the amount of the carboxylic acid remaining after the reaction, is more preferred to be 0.45 to 0.5 mole.

When the use amount of the sulfonyl halide compound is less than 0.4 mole per mole of the carboxylic acid, the yield of the acid anhydride obtained tends to be low. When the use amount of the sulfonyl halide compound is more than 0.6 mole per mole of the carboxylic acid, the unreacted sulfonyl halide compound remains in the acid anhydride obtained and the purity of the acid anhydride obtained tends to be low.

In the reaction, use of a solvent is not essential. However, the reaction is preferred to be conducted in the presence of a solvent. The solvent used in the reaction may be any solvent as long as it does no react with the raw materials or the reaction products. When after the completion of the reaction, the reaction mixture is washed with water for separation of impurities, it is preferred to use a water-insoluble solvent. Use of this water-insoluble solvent can eliminate the operation of solvent replacement before the water washing.

As specific examples of the solvent used in the reaction, there can be shown aromatic solvents such as benzene, toluene, xylene and the like; ether type solvents such as diethyl ether, tetrahydrofuran and the like; ester type solvents such as ethyl acetate, butyl acetate and the like; and halogen-containing solvents such as methylene chloride, chloroform, trichloroethane, ethylene dichloride and the like.

Of these solvents, a solvent having a boiling point lower than that of the acid anhydride obtained is used preferably. By using such a solvent, it is easy to concentrate the reaction mixture obtained after the reaction. When after the reaction, the reaction mixture is washed with water in order to separate the salts formed as by-products, it is preferred to use a solvent enabling azeotropy with water, such as toluene, methylene chloride and chloroform. By using such a solvent, water removal is also possible at the time of solvent removal by distillation.

The concentration of the carboxylic acid when added to the solvent is preferably 25 to 50% by mass for easy stirring.

When there is used, as the carboxylic acid, a carboxylic acid having a polymerizable group, such as acrylic acid or methacrylic acid, it is preferred to allow a polymerization inhibitor to co-exist in the reaction system. The polymerization inhibitor may be any polymerization inhibitor as long as it does not react with the reaction raw materials or the reaction products.

As specific examples of the polymerization inhibitor, there can be shown p-methoxyphenol, hydroquinone, phenothiazine, tetramethylpiperazine oxyl, Sumilizer GM, Sumilizer TP-D and Sumilizer WX-R [Sumilizers (trade name) are produced by Sumitomo Chemical Co., Ltd.].

The use amount of the polymerization inhibitor is preferably 0.01 to 5% by mass based on the mass of the carboxylic acid.

As to the order of feeding the raw materials, there is no restriction, and any order may be used or all the raw materials may be fed at once. However, when the sulfonyl halide compound and the inorganic base or the tertiary amine are fed first, they react with each other partially, which tends to give a reduced yield. Therefore, it is preferred to fed the carboxylic acid and the sulfonyl halide compound prior to mixing of the above raw materials.

In an appropriate order, the tertiary amine is mixed with a mixture of the carboxylic acid and the sulfonyl halide compound. When, in the reaction, the inorganic base is used in combination with the tertiary amine, the addition timing of the inorganic base is preferably simultaneous with the addition of the tertiary amine, or before or after the addition. When the inorganic base is used together, it is preferred that for a stable and efficient reaction, part of the carboxylic acid fed and part of the sulfonyl halide compound fed are first reacted with each other in the presence of the tertiary amine and then the inorganic base is added.

The most practical feeding order for carrying out the reaction efficiently is shown below. (1) A solvent, (2) a polymerization inhibitor when there is used a carboxylic acid having a polymerizable group, (3) a carboxylic acid and (4) a sulfonyl halide compound are fed in this order; the mixture is kept at an appropriate reaction temperature; then, (5) a tertiary amine is added dropwise; thereafter, (5) an inorganic base is added to start a reaction.

The dropping time of the tertiary amine differs depending upon the kinds of the solvent, carboxylic acid and sulfonyl halide compound used and therefore is appropriately selected ordinarily in a range of 1 to 3,000 minutes.

When the inorganic base is used in combination with the tertiary amine, the amount of heat generated in the reaction is smaller than when the tertiary amine is used alone. Therefore, the addition time of the inorganic base is appropriately selected ordinarily in a range of 1 to 2,500 minutes, depending upon the kinds of the carboxylic acid, sulfonyl halide compound and solvent used.

The reaction temperature differs depending upon the kind of the tertiary amine used; however, it is in a range of preferably −100° C. to the boiling point of the solvent, more preferably −70° C. to 90° C. In the production process of the present invention, the use amount of the tertiary amine is smaller than in conventional processes; therefore, the reaction proceeds mildly. Hence, cooling to ice point or lower as in conventional processes is not required and yet the reaction proceeds relatively mildly. Particularly in a mode for carrying out the reaction with a particular amount of the inorganic base being allowed to co-exist, the reaction is milder and can be carried out in a specific range of 5 to 30° C. By employing this reaction temperature, the production of the acid anhydride is advantageous with respect to the production facility and energy required.

The reaction time is appropriately selected considering the reaction temperature employed and the stability of the carboxylic acid used. When the tertiary amine is used alone, the reaction time is preferred to be generally about 0.1 to 10 hours after the addition of the tertiary amine. When the reaction is conducted in a state that the inorganic base is used in combination and the use amount of the tertiary amine is reduced, the reaction proceeds more mildly as mentioned previously; in this case, therefore, the reaction time is longer than when the tertiary amine is used alone. When both the tertiary amine and the inorganic base are used, the reaction time is preferred to be generally 0.5 to 50 hours after the addition of the two compounds.

The reaction may ordinarily be conducted under pressure or under reduced pressure.

As the method for separating, after the completion of the reaction, a salt (a by-product) generated from the sulfonyl halide compound and a salt (a by-product) generated from the tertiary amine, there is preferred an extraction method of washing the reaction mixture with water.

The details of the washing of the reaction mixture with water differ depending upon the reaction system used; therefore, the use amount of water, the times of washing, etc. are determined appropriately. In the second or later washing, it is possible to use, in place of water, an aqueous sodium hydrogencarbonate solution, an aqueous sodium carbonate solution, an aqueous sodium hydroxide solution, an aqueous potassium hydrogencarbonate solution, an aqueous potassium carbonate solution, an aqueous potassium hydroxide solution or the like to remove the remaining carboxylic acid and sulfonyl halide compound. In this case, in order to avoid decomposition of the acid anhydride (intended product), it is necessary to determine the alkali concentration in washing solution, the use amount of alkali, and the times of washing in thorough consideration of the stability of the acid anhydride obtained.

It is possible to add, to the aqueous phase containing salts (by-products), generated from the washing operation, a strong alkali such as sodium hydroxide, potassium hydroxide, calcium hydroxide, lithium hydroxide or the like to liberate triethylamine, then recover the triethylamine from the aqueous phase by extraction, distillation or the like, and use the recovered triethylamine in the next production.

Alternatively, the salts (by-products) may be removed by a solid-liquid separation method. As the solid-liquid separation method, filtration and decantation can be mentioned.

The reaction mixture after the filtration or decantation may be washed with water as necessary.

The acid anhydride-containing solution after the washing or the solid-liquid separation is as necessary dehydrated by a dehydrating agent such as anhydrous sodium sulfate, magnesium sulfate, calcium chloride or the like. Then, distillation under reduced pressure is conducted, whereby the solvent present in the dehydrated solution can be removed. The degree of reduced pressure and the distillation temperature may be appropriately selected depending upon the boiling point of the carboxylic acid anhydride obtained and the boiling point of the solvent used.

When the temperature of reduced pressure distillation or the degree of reduced pressure is too high, the obtained carboxylic anhydride per se is distilled, which may reduce the yield. Therefore, care must be taken.

The carboxylic acid anhydride obtained is subjected as necessary to reduced pressure distillation for purification. The degree of reduced pressure and the temperature of reduced pressure distillation are appropriately selected depending upon the kind of the acid anhydride obtained, in view of the boiling point of the acid anhydride.

EXAMPLES

The present invention is described more specifically below by way of Examples. However, the present invention is in no way restricted to these Examples.

Example 1

In a 3-liter, four-necked glass reactor provided with a thermometer and a stirrer were placed, in a nitrogen atmosphere, 1,240 g of methylene chloride, 1.08 g (0.5% by mass) of Sumilizer GM, 0.65 g (0.3% by mass) of Sumilizer TP-D, 0.65 g (0.3% by mass) of Sumilizer WX-R (each Sumilizer is a trade name and a polymerization inhibitor produced by Sumitomo Chemical Co., Ltd.), 216 g (3.0 mol) of acrylic acid and 172 g (1.5 mol) of methanesulfonyl chloride. The mixture was cooled to 5° C.

Then, 304 g (3.0 mol, 1 equivalent relative to the acids generated from methanesulfonyl chloride) of triethylamine was dropwise added in 2 hours with the temperature of the reaction mixture being controlled at 30° C. or lower. After the completion of the dropwise addition, stirring was made for 1 hour with the same temperature being kept. The reaction mixture was analyzed by a gas chromatograph (GC), which indicated that the conversion of acrylic acid was 99%.

After the completion of the reaction, 375 g of water was added to the reaction mixture to wash the reaction mixture. The reaction mixture was further washed twice each time with 563 g of water, after which distillation was conducted to remove methylene chloride. The yield of the acrylic acid anhydride obtained was 172 g and 91% and its purity by GC analysis was 98%, and no high-molecular by-product was detected. The identification of acrylic acid anhydride was conducted by analyses of nuclear magnetic resonance spectrum, elemental analysis data, and mass spectrum. The same analytical techniques were used also in later Examples and Comparative Examples to determine various values.

Comparative Example 1

A reaction was conducted in accordance with Example 1 except that the amount of triethylamine used in Example 1 was changed to 455 g (4.5 mol, 1.5 equivalents relative to the acids generated from methanesulfonyl chloride).

Acrylic acid anhydride could be produced at an acrylic acid conversion of 99%, at a yield of 150 g and 79%, and at a purity (determined by GC analysis) of 74%. The amount of high-molecular by-products formed was 20%.

Example 2

In a 3-liter, four-necked glass reactor provided with a thermometer and a stirrer were placed, in a dry air atmosphere, 1,240 g of methylene chloride, 1.08 g (0.5% by mass) of Sumilizer GM, 0.65 g (0.3% by mass) of Sumilizer TP-D, 0.65 g (0.3% by mass) of Sumilizer WX-R (each Sumilizer is a trade name and a polymerization inhibitor produced by Sumitomo Chemical Co., Ltd.), 216 g (3.0 mol) of acrylic acid and 264 g (1.5 mol) of benzenesulfonyl chloride. The mixture was cooled to 5° C.

Then, 304 g (3.0 mol, 1 equivalent relative to the acids generated from benzenesulfonyl chloride) of triethylamine was dropwise added in 2 hours with the temperature of the reaction mixture being controlled at 30° C. or lower. After the completion of the dropwise addition, stirring was made for 1 hour with the same temperature being kept. The reaction mixture was analyzed by GC, which indicated that the conversion of acrylic acid was 99%.

After the completion of the reaction, 375 g of water was added to the reaction mixture to wash the reaction mixture. The reaction mixture was further washed twice each time with 563 g of water, after which distillation was conducted to remove methylene chloride. The yield of the acrylic acid anhydride obtained was 172 g and 91% and its purity by GC analysis was 99%, and no high-molecular by-product was detected.

Example 3

In a 3-liter, four-necked glass reactor provided with a thermometer and a stirrer were placed, in a nitrogen atmosphere, 1,000 g of toluene, 1.29 g (0.5% by mass) of Sumilizer GM, 0.77 g (0.3% by mass) of Sumilizer TP-D, 0.77 g (0.3% by mass) of Sumilizer WX-R (each Sumilizer is a trade name and a polymerization inhibitor produced by Sumitomo Chemical Co., Ltd.), 258 g (3.0 mol) of methacrylic acid and 286 g (1.5 mol) of p-toluenesulfonyl chloride. The mixture was cooled to 10° C.

Then, 304 g (3.0 mol, 1 equivalent relative to the acids generated from p-toluenesulfonyl chloride) of triethylamine was dropwise added in 2 hours with the temperature of the reaction mixture being controlled at 30° C. or lower. After the completion of the dropwise addition, stirring was made for 1 hour with the same temperature being kept. The reaction mixture was analyzed by GC, which indicated that the conversion of methacrylic acid was 99%.

After the completion of the reaction, 375 g of water was added to the reaction mixture to wash the reaction mixture. The reaction mixture was further washed twice each time with 563 g of water, after which distillation was conducted to remove toluene. The yield of the methacrylic acid anhydride obtained was 208 g and 90% and its purity by GC analysis was 98%, and no high-molecular by-product was detected.

Example 4

In a 3-liter, four-necked glass reactor provided with a thermometer and a stirrer were placed, in a nitrogen atmosphere, 1,000 g of toluene, 1.29 g (0.5% by mass) of Sumilizer GM, 0.77 g (0.3% by mass) of Sumilizer TP-D, 0.77 g (0.3% by mass) of Sumilizer WX-R (each Sumilizer is a trade name and a polymerization inhibitor produced by Sumitomo Chemical Co., Ltd.), 258 g (3.0 mol) of methacrylic acid and 265 g (1.5 mol) of benzenesulfonyl chloride. The mixture was cooled to 10° C.

Then, 304 g (3.0 mol, 1 equivalent relative to the acids generated from benzenesulfonyl chloride) of N-methylmorpholine was dropwise added in 2 hours with the temperature of the reaction mixture being controlled at 30° C. or lower. After the completion of the dropwise addition, stirring was made for 1 hour with the same temperature being kept. The reaction mixture was analyzed by GC, which indicated that the conversion of methacrylic acid was 99%.

After the completion of the reaction, 375 g of water was added to the reaction mixture to wash the reaction mixture. The reaction mixture was further washed twice each time with 563 g of water, after which distillation was conducted to remove toluene. The yield of the methacrylic acid anhydride obtained was 208 g and 90% and its purity by GC analysis was 98%, and no high-molecular by-product was detected.

Examples 5 to 16

Operations were conducted in the same manner as in Example 4 except that the solvent, carboxylic acid and tertiary amine shown in Table 1 were used in respective amounts shown in Table 1. The results obtained are shown in Table 1.

Comparative Examples 2 and 3

Operations were conducted in the same manner as in Example 14 except that the amount of N-methylmorpholine used in Example 14 was changed to 455 g (4.5 mol, 1.5 equivalents relative to the acids generated from methanesulfonyl chloride) or 202 g (2.0 mol, 0.67 equivalent relative to the acids generated from methanesulfonyl chloride).

The results obtained are shown in Table 1.

TABLE 1

| | Solvent | Carboxylic acid | Tertiary amine equivalent* | Conversion % | Yield g | Yield % | Purity % | High-molecular compound % |
|---|---|---|---|---|---|---|---|---|
| Ex. 5 | Methylene chloride | Crotonic acid | Triethylamine 1.0 | 98 | 208 | 90 | 96 | 0 |
| Ex. 6 | Ethyl acetate | Pivalic acid | N-methylmorpholine 1.0 | 97 | 249 | 89 | 97 | 0 |
| Ex. 7 | Toluene | Cyclopropane-carboxylic acid | N-ethylmorpholine 1.0 | 97 | 208 | 90 | 97 | 0 |
| Ex. 8 | Chloroform | Cyclobutane-carboxylic acid | Tributylamine 1.0 | 97 | 243 | 89 | 96 | 0 |
| Ex. 9 | Tetrahydrofuran | Tetrahydrofuran-carboxylic acid | Pyridine 1.0 | 98 | 289 | 90 | 96 | 0 |
| Ex. 10 | Methylene chloride | trans-cinnamic acid | N-methylpyrrolidine 1.0 | 97 | 371 | 89 | 96 | 0 |
| Ex. 11 | Methylene chloride | 3-Methylcrotonic acid | N-methylpiperidine 1.0 | 97 | 243 | 89 | 96 | 0 |
| Ex. 12 | Methylene chloride | α-Pyromucic acid | Triethylamine 1.0 | 96 | 276 | 89 | 96 | 0 |
| Ex. 13 | Methylene chloride | p-Nitrobenzoic acid | Triethylamine 1.0 | 96 | 435 | 89 | 96 | 0 |
| Ex. 14 | Toluene | Propionic acid | N-methylmorpholine 0.92 | 96 | 173 | 89 | 96 | 0 |
| Ex. 15 | Toluene | Methacrylic acid | N-methylmorpholine 0.92 | 92 | 171 | 88 | 95 | 0 |
| Ex. 16 | Toluene | Methacrylic acid | N-methylmorpholine 1.09 | 97 | 171 | 88 | 95 | 0 |
| Comp. Ex. 2 | Toluene | Propionic acid | N-methymorpholine 1.5 | 96 | 160 | 82 | 86 | 0 |
| Comp. Ex. 3 | Toluene | Propionic acid | N-methylmorpholine 0.67 | 80 | 136 | 70 | 84 | 0 |

*Equivalent relative to the acids generated from sulfonic acid halide.

Example 17

In a 3-liter, four-necked glass reactor provided with a thermometer and a stirrer were placed, in a nitrogen atmosphere, 1,240 g of toluene, 1.08 g (0.5% by mass) of Sumilizer GM, 0.65 g (0.3% by mass) of Sumilizer TP-D, 0.65 g (0.3% by mass) of Sumilizer WX-R (each Sumilizer is a trade name and a polymerization inhibitor produced by Sumitomo Chemical Co., Ltd.), 258 g (3.0 mol) of methacrylic acid and 172 g (1.5 mol) of methanesulfonyl chloride. The mixture was cooled to 5° C.

Then, 30 g (0.3 mol, 0.1 equivalent relative to the acids generated from benzenesulfonyl chloride) of N-methylmorpholine was dropwise added in 30 minutes with the temperature of the reaction mixture being controlled at 30° C. or lower. Further, 148 g (1.4 mol, 0.93 equivalent relative to the acids generated from methanesulfonyl chloride) of sodium carbonate was added. Then, stirring was made for 10 hours with the same temperature being kept. The reaction mixture was analyzed by GC, which indicated that the conversion of methacrylic acid was 99%.

After the completion of the reaction, 500 g of water was added to the reaction mixture to wash the reaction mixture. The reaction mixture was further washed twice each time with 563 g of water, after which distillation was conducted to remove methylene chloride. The yield of the methacrylic acid anhydride obtained was 217 g and 94% and its purity by GC analysis was 98%, and no high-molecular by-product was detected.

Example 18

In a 3-liter, four-necked glass reactor provided with a thermometer and a stirrer were placed, in a nitrogen atmosphere, 1,240 g of methylene chloride, 1.08 g (0.5% by mass) of Sumilizer GM, 0.65 g (0.3% by mass) of Sumilizer TP-D, 0.65 g (0.3% by mass) of Sumilizer WX-R (each Sumilizer is a trade name and a polymerization inhibitor produced by Sumitomo Chemical Co., Ltd.), 216 g (3.0 mol) of acrylic acid and 265 g (1.5 mol) of benzenesulfonyl chloride. The mixture was cooled to 5° C.

Then, 30 g (0.3 mol, 0.1 equivalent relative to the acids generated from methanesulfonyl chloride) of triethylamine was dropwise added in 30 minutes with the temperature of the reaction mixture being controlled at 30° C. or lower. Further, 148 g (1.4 mol, 0.93 equivalent relative to the acids generated from benzenesulfonyl chloride) of sodium carbonate was added. Then, stirring was made for 10 hours with the same temperature being kept. The reaction mixture was analyzed by GC, which indicated that the conversion of acrylic acid was 99%.

After the completion of the reaction, 500 g of water was added to the reaction mixture to wash the reaction mixture. The reaction mixture was further washed twice each time with 563 g of water, after which distillation was conducted to remove methylene chloride. The yield of the acrylic acid anhydride obtained was 180 g and 95% and its Operations were conducted in the same manner as in Example 23 except that the amount of sodium carbonate used in Example 23 was changed to 212 g (2.0 mol, 1.33 equivalents relative to the acids generated from methanesulfonyl chloride, 1.43 equivalents together with triethylamine) or 95 g (0.9 mol, 0.6 equivalent relative to the acids generated from methanesulfonyl chloride, 0.7 equivalent together with triethylamine). The results obtained are shown in Table 2.

Comparative Example 9

An operation was conducted in the same manner as in Example 23 except that the amount of triethylamine used in Example 23 was changed to 9.1 g (0.09 mol, 0.03 equivalent relative to the acids generated from methanesulfonyl chloride) and the amount of sodium carbonate used in Example 23 was changed to 154 g (1.455 mol, 0.97 equivalent relative to the acids generated from methanesulfonyl chloride). The results obtained are shown in Table 2.

TABLE 2

| | Carboxylic acid | Tertiary amine Equivalent* | Inorganic base equivalent* | Conversion % | Yield g | Yield % | Purity % | High-molecular compound % |
|---|---|---|---|---|---|---|---|---|
| Ex. 19 | Crotonic acid | Triethylamine 0.1 | Sodium hydrogencarbonate 0.93 | 97 | 215 | 93 | 98 | 0 |
| Ex. 20 | Pivalic acid | N-methylmorpholine 0.1 | Potassium carbonate 0.93 | 97 | 263 | 94 | 98 | 0 |
| Ex. 21 | Cyclopropanecarboxylic acid | N-ethylmorpholine 0.1 | Potassium hydrogencarbonate 0.93 | 97 | 217 | 94 | 98 | 0 |
| Ex. 22 | Cyclobutanecarboxylic acid | Tributylamine 0.1 | Calcium carbonate 0.93 | 98 | 254 | 93 | 98 | 0 |
| Ex. 23 | Tetrahydrofurancarboxylic acid | Triethylamine 0.1 | Sodium carbonate 0.93 | 98 | 302 | 94 | 98 | 0 |
| Ex. 24 | Acrylic acid | Triethylamine 0.3 | Sodium carbonate 0.75 | 97 | 299 | 93 | 98 | 0 |
| Ex. 25 | Acrylic acid | Triethylamine 0.5 | Sodium carbonate 0.59 | 97 | 296 | 92 | 96 | 0 |
| Ex. 26 | Acrylic acid | Triethylamine 0.25 | Sodium carbonate 0.8 | 97 | 296 | 92 | 96 | 0 |
| Comp. Ex. 4 | Acrylic acid | Triethylamine 0.1 | Sodium carbonate 1.33 | 96 | 153 | 81 | 89 | 5 |
| Comp. Ex. 5 | Acrylic acid | Triethylamine 0.1 | Sodium carbonate 0.6 | 80 | 152 | 80 | 88 | 0 |
| Comp. Ex. 6 | Acrylic acid | Triethylamine 0.03 | Sodium carbonate 0.97 | 68 | 106 | 56 | 88 | 0 |
| Comp. Ex. 7 | Tetrahydrofurancarboxylic acid | Triethylamine 0.1 | Sodium carbonate 1.33 | 96 | 270 | 84 | 89 | 1 |
| Comp. Ex. 8 | Tetrahydrofurancarboxylic acid | Triethylamine 0.1 | Sodium carbonate 0.6 | 75 | 215 | 67 | 88 | 0 |
| Comp. Ex. 9 | Tetrahydrofurancarboxylic acid | Triethylamine 0.03 | Sodium carbonate 0.97 | 68 | 175 | 55 | 88 | 0 |

*Equivalent relative to the acids generated from sulfonic acid halide.

purity by GC analysis was 98%, and no high-molecular by-product was detected.

Examples 19-26

Operations were conducted in the same manner as in Example 18 except that the inorganic base, carboxylic acid and tertiary amine shown in Table 2 were used in respective amounts shown in Table 2. The results obtained are shown in Table 2.

Comparative Examples 4 and 5

Operations were conducted in the same manner as in Example 18 except that the amount of sodium carbonate used in Example 18 was changed to 212 g (2.0 mol, 1.33 equivalents relative to the acids generated from methanesulfonyl chloride, 1.43 equivalents together with triethylamine) or 95 g (0.9 mol, 0.6 equivalent relative to the acids generated from methanesulfonyl chloride, 0.7 equivalent together with triethylamine). The results obtained are shown in Table 2.

Comparative Example 6

An operation was conducted in the same manner as in Example 18 except that the amount of triethylamine used in Example 18 was changed to 9.1 g (0.09 mol, 0.03 equivalent relative to the acids generated from methanesulfonyl chloride) and the amount of sodium carbonate used in Example 18 was changed to 154 g (1.455 mol, 0.97 equivalent relative to the acids generated from methanesulfonyl chloride). The results obtained are shown in Table 2.

Comparative Examples 7 and 8

According to the present invention, in reacting a carboxylic acid with a sulfonyl halide in the presence of a tertiary amine, the amount of the tertiary amine used is specified in a particular range; thereby, the reaction becomes mild and resultantly an acid anhydride of high purity can be produced at a high yield while the formation of the impurities being suppressed. When an inorganic base is used together with the tertiary amine, the reaction becomes milder and an acid anhydride of high purity can be produced at a high yield.

Further, since the amount of the triethylamine remaining in the reaction mixture after the reaction is small, there are improvements in the purification of the acid anhydride produced as well as in the operation of waste solution disposal.

The invention claimed is:

1. A process for producing an acrylic acid anhydride or methacrylic acid anhydride by reacting an acrylic acid or a methacrylic acid with a sulfonyl halide compound in the presence of a tertiary amine, wherein the amount of the tertiary amine used is 0.9 to 1.2 equivalents relative to the acid generated from the sulfonyl halide compound.

2. A process for producing an acid anhydride according to claim 1, wherein the amine is a tertiary amine wherein alkyl groups of 2 to 4 carbon atoms are bonded to a nitrogen atom, or a cyclic amine.

3. A process for producing an acid anhydride according to claim 1, wherein the sulfonyl halide compound is a compound represented by the following formula (2)

(wherein $R^2$ is an alkyl group, a cycloalkyl group, an aralkyl group or an aryl group, and X is a halogen atom).

4. A process for producing an acrylic acid anhydride or methacrylic acid anhydride by reacting an acrylic acid or a methacrylic acid with a sulfonyl halide compound in the presence of a tertiary amine and an inorganic base, wherein the total amount of the tertiary amine and inorganic base used is 0.9 to 1.2 equivalents relative to the acid generated from the sulfonyl halide compound and at least 0.05 equivalent in the total amount used is the amount of the tertiary amine.

5. A process for producing an acid anhydride according to claim 4, wherein the amine is a tertiary amine wherein alkyl groups of 2 to 4 carbon atoms are bonded to the nitrogen atom, or a cyclic amine.

6. A process for producing an acid anhydride according to claim 4, wherein the sulfonyl halide compound is a compound represented by the following formula (2)

(wherein $R^2$ is an alkyl group, a cycloalkyl group, an aralkyl group or an aryl group, and X is a halogen atom).

* * * * *